United States Patent [19]

Wong et al.

[11] Patent Number: 5,417,682
[45] Date of Patent: May 23, 1995

[54] DEVICE FOR ADMINISTERING ACTIVE AGENT TO BIOLOGICAL ENVIRONMENT

[75] Inventors: Patrick S. L. Wong, Palo Alto; Felix Theeuwes, Los Altos Hills; Steven D. Larsen, Dublin; Liang C. Dong, Mountain View, all of Calif.

[73] Assignee: Alza Corporation, Palo Alto, Calif.

[21] Appl. No.: 186,046

[22] Filed: Jan. 21, 1994

Related U.S. Application Data

[63] Continuation-in-part of Ser. No. 830,160, Jan. 31, 1992, Pat. No. 5,312,388, which is a continuation-in-part of Ser. No. 648,270, Jan. 30, 1991, abandoned.

[51] Int. Cl.$^6$ ............................................. A61K 9/22
[52] U.S. Cl. ................................................ 604/892.1
[58] Field of Search ............... 604/890.1, 891.1, 892.1, 604/246; 424/457, 468

[56] References Cited

U.S. PATENT DOCUMENTS 4,034,756 7/1977 Higuchi et al. ..................... 128/260

Primary Examiner—C. Fred Rosenbaum
Assistant Examiner—Manuel Mendez
Attorney, Agent, or Firm—Paul L. Sabatine; Alisa A. Harbin; Felissa H. Cagan

[57] ABSTRACT

The present invention is directed to a fluid-imbibing dispensing device for the immediate or almost immediate and extended delivery of an active agent over a prolonged period of time together with the initially delayed pulse delivery of an active agent to a fluid environment of use. The dispenser comprises a housing having a first wall section and a second wall section in slidably telescoping arrangement with each other, which housing maintains its integrity in the environment of use; an internal compartment surrounded and defined by the housing; a first active agent delivery chamber within a portion of the compartment defined by the first wall section, the first delivery chamber including at least one active agent formulation, an exit means for providing communication between the active agent formulation and the environment, and a first expansion means for dispensing the first active agent formulation through the exit means to the environment immediately and over a prolonged period of time; a second active agent delivery chamber within a portion of the compartment defined by the first wall section and adjacent the open end of the first wall section, the second delivery chamber including at least one active agent formulation; and an expansion chamber within a portion of the compartment defined by the second wall section, for separating apart the first and second wall sections of the housing after exposure to the environment of use for dispensing the second active agent formulation to the environment in a pulse after an initially delayed period of time, the expansion chamber including a second expansion means and a partition layer or push plate.

7 Claims, 4 Drawing Sheets

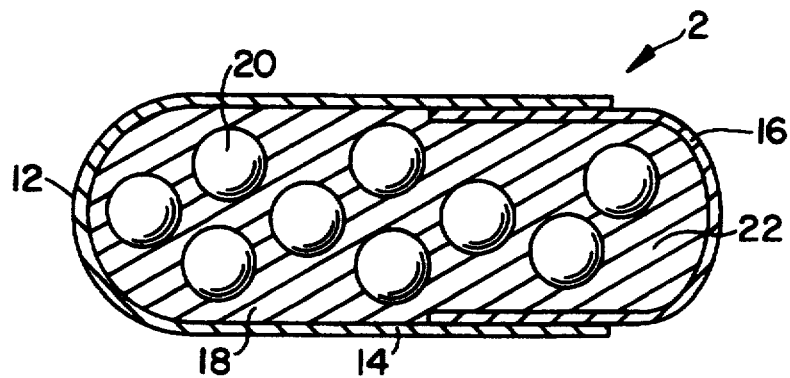
FIG. 4
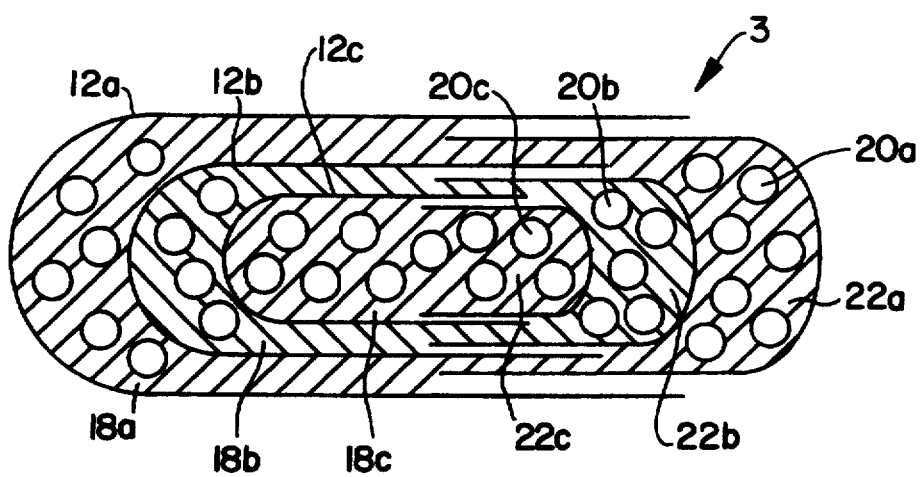
FIG. 5
FIG. 6
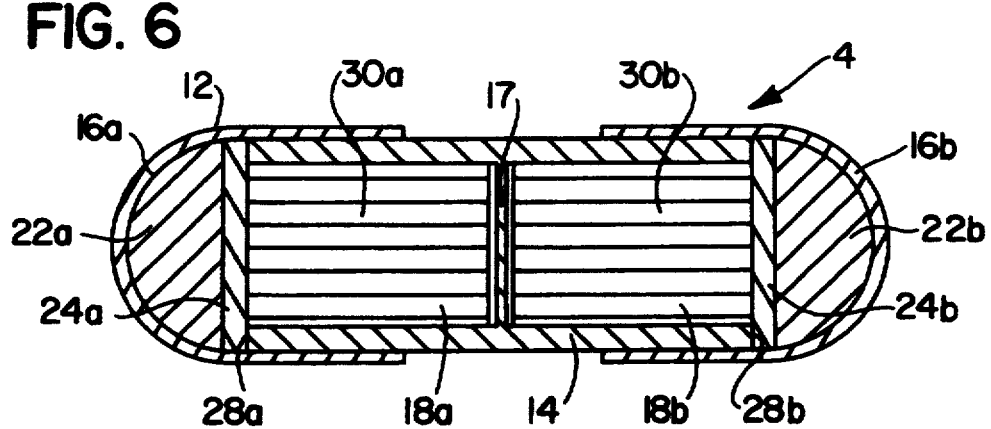

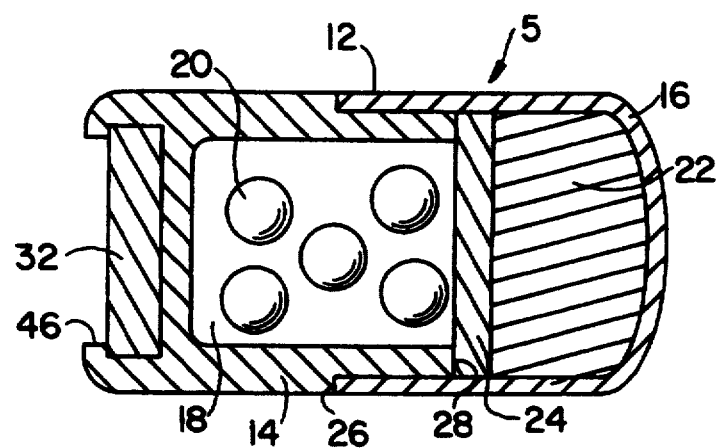
FIG. 7
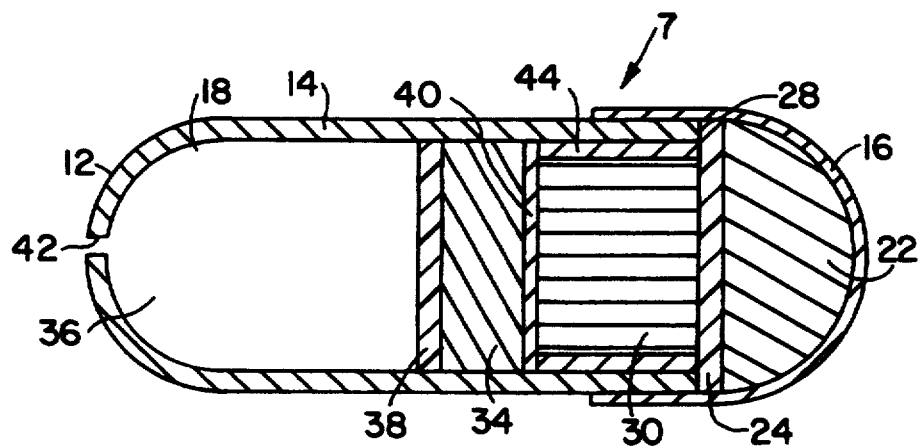
FIG. 9
FIG. 10
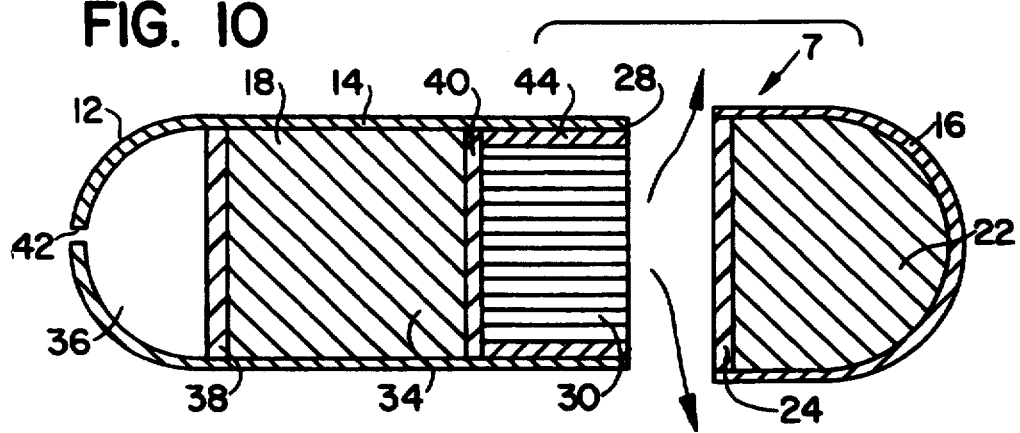

DEVICE FOR ADMINISTERING ACTIVE AGENT TO BIOLOGICAL ENVIRONMENT

CROSS-REFERENCE TO RELATED APPLICATION

This application is a continuation-in-part of U.S. application Ser. No. 07/830,160 filed Jan. 31, 1992, now U.S. Pat. No. 5,312,388 issued May 17, 1994, which application Ser. No. 07/830,160 is a continuation-in-part of U.S. application Ser. No. 07/648,270 filed Jan. 30, 1990 now abandoned; application Ser. No. 07/830,160 is copending with U.S. application Ser. No. 08/109,120 filed Aug. 19, 1993, which Ser. No. 08/109,120 is a continuation-in-part of Ser. No. 07/648,270; which applications are incorporated herein by reference and benefit is claimed of their filing dates.

FIELD OF THE INVENTION

The present invention is related to the delayed delivery of an active agent. More particularly, it is related to osmotically-activated devices for dispensing active agents to a biological environment of use following an initial delay.

BACKGROUND OF THE INVENTION

Osmotic dispensing devices for delivery of therapeutically active agents are well known in the art. Such devices use an expansion means to deliver an agent to an environment of use over a period of hours, days or months. The expansion means absorbs liquid, expands, and acts to drive out beneficial agent formulation from the interior of the device in a controlled, usually constant manner. The osmotic expansion means is used to controllably, usually relatively slowly, and over a period of time, deliver the agent. Thus, these devices are not generally used to delay the initial release of the agent, followed by the rapid release, or substantially simultaneous introduction, of all of the agent or all of the dosage form(s) containing the agent into the environment of use at one time.

The delay of the initial release of an agent has primarily been previously effected by coating the agent or a formulation containing the agent with a dissolvable or bioerodible coating layer, such as gelatin, which coating dissolves or erodes in the environment of use to then make the agent available. Delayed initial release has also been provided by dispersing the agent in a dissolvable or erodible matrix. However, such systems are often unreliable and release cannot be controlled with great accuracy due to the variability and relatively uncontrollable nature of erosion and dissolution.

Therefore, there remains a continuing need for improved methods and systems for providing a delayed initial delivery of an active agent to an environment of use that are reliable and that can be programmed to deliver the agent after a particular interval with increased accuracy. In addition, there is a need for systems which provide a delayed, pulse delivery of an agent together with an immediate delivery of another agent, delivery of this other agent being over a prolonged period of time.

SUMMARY OF THE INVENTION

The present invention is directed to a fluid-imbibing dispensing device for the immediate or almost immediate and extended delivery of an active agent over a prolonged period of time together with the initially delayed pulse delivery of an active agent to a fluid environment of use. The dispenser comprises a housing having a first wall section and a second wall section in slidably telescoping arrangement with each other, which housing maintains its integrity in the environment of use; an internal compartment surrounded and defined by the housing; a first active agent delivery chamber within a portion of the compartment defined by the first wall section, the first delivery chamber including at least one active agent formulation, an exit means for providing communication between the active agent formulation and the environment, and a first expansion means for dispensing the first active agent formulation through the exit means to the environment immediately and over a prolonged period of time; a second active agent delivery chamber within a portion of the compartment defined by the first wall section and adjacent the open end of the first wall section, the second delivery chamber including at least one active agent formulation; and an expansion chamber within a portion of the compartment defined by the second wall section, for separating apart the first and second wall sections of the housing after exposure to the environment of use for dispensing the second active agent formulation to the environment in a pulse after an initially delayed period of time, the expansion chamber including a second expansion means and a partition layer or push plate.

The invention also is directed to a method for delaying the initial delivery of an active agent to a fluid environment of use while at the same time delivering another active agent to the environment immediately and over a prolonged period, the method comprising placing the dispensing device of the invention into the environment of use, allowing fluid to be imbibed through at least a portion of the housing of the dispensing device for causing the first expansion means to expand to deliver a first agent formulation into the environment immediately and for a prolonged period of time and for causing the second expansion means to expand and exert pressure on the slidably connected first and second wall sections to push apart and separate the two wall sections to deliver a second agent formulation to the environment after an initially delayed period of time. During the delay period in the environment, the volume of the second active agent delivery chamber containing the second active agent is kept constant; therefore, there is a negligible pressure gradient between the environment and the interior of the second delivery chamber. As a result, net flow of the environmental fluid driven by the pressure to enter the second delivery chamber is minimal, so that the active agent is not contaminated or diluted.

DESCRIPTION OF THE DRAWINGS

The drawings are not drawn to scale, but are set forth to illustrate various embodiments of the invention. Like numbers refer to like structures.

FIG. 4 is a cross-sectional view of another embodiment of the present invention, in closed or prepared form.

FIG. 5 is a cross-sectional view of yet another embodiment of the present invention, directed to a multi-pulse dispensing device.

FIG. 6 is a cross-sectional view of an embodiment of the present invention directed to a multi-agent and/or multi-pulse dispensing device.

FIG. 7 is a cross-sectional view of an embodiment of the present invention which includes a loading dose for the initial rapid delivery of an agent together with an initial delayed delivery of another agent.

FIG. 9 is a cross-sectional view of the embodiment of FIG. 8, after activation, at a point in time when the device is opened to release the second active agent.

FIG. 10 is a cross-sectional view of another embodiment of the present invention, related to the embodiment of FIGS. 8 and 9.

DETAILED DESCRIPTION OF THE INVENTION

The present invention provides a device which is useful for the initial delayed delivery of an active agent formulation to a fluid environment of use, the delivery of the agent formulation from the dispensing device, once begun, being quickly completed. At the same time, the device delivers another active agent formulation to the environment without an initial delay, delivery of this other active agent formulation being continued over a prolonged period of time. By "prolonged period of time" is meant an extended time period such as for several hours, days, weeks or months. The delivery device of this invention is designed to, at a first time $t_a$ immediately or almost immediately after introduction to a fluid environment, begin delivery of the first agent formulation, the delivery continuing for an extended period of time $t_b$, and also to, at a second time $t_c$ which is some predetermined time after introduction of the device to the fluid environment, substantially simultaneously introduce all of the second active agent formulation, which formulation can be either an immediate release dosage form or a controlled release dosage form, to exposure to the environment of use substantially at one time after the initial period of delay $t_c$. The time of delay $t_c$ is preset and may be some time during the prolonged delivery period $t_b$ or it may be at a time after the prolonged delivery period $t_b$ has passed.

As used herein, the terms "therapeutically effective" amount or rate refer to the amount or rate of the active agent needed to effect the desired therapeutic, often beneficial, result.

The dispensing devices of the invention find use, for example, in humans or other animals. The environment of use is a fluid environment and can comprise the stomach, the intestinal tract, or a body cavity such as the peritoneum or vagina. A single dispensing device or several dispensing devices can be administered to a subject during a therapeutic program.

Figure 1:
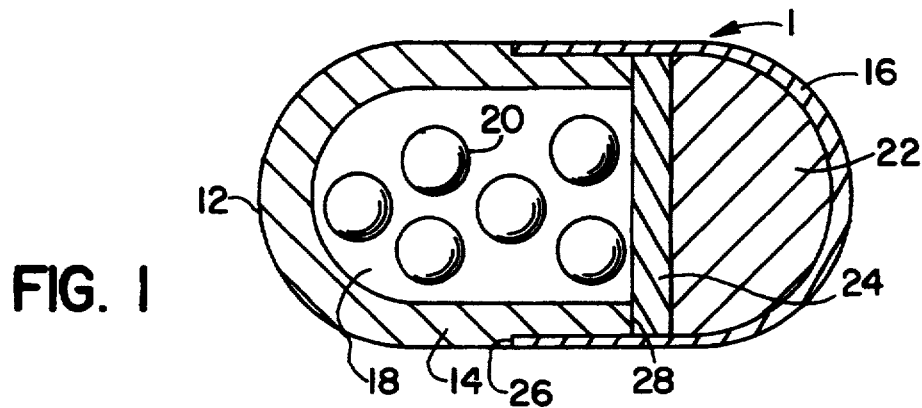
FIG. 1 is a cross-sectional view of one embodiment of the present invention, the device being in closed or prepared form prior to placement in the environment of use.

FIG. 1 depicts in cross-sectional view a presently preferred embodiment of the delivery device according to the present invention. The device is shown in closed or prepared form prior to placement in the environment of use. Dispensing device 1 comprises a housing 12 formed of a first wall section 14 and a second wall section 16. First wall section 14 and second wall section 16 are in slidably telescoping arrangement with each other. Housing 12 surrounds and defines an internal compartment 18. First wall section 14 surrounds that portion of internal compartment 18 that contains an active agent formulation, in this embodiment the formulation being a plurality of active agent dosage forms 20. Second wall section 16 surrounds that portion of internal compartment 18 that contains an expansion means 22 for expanding and for occupying space in compartment 18. Second wall section 16 also contains a partition layer 24, which layer 24 is positioned between the agent formulation 20 and the expansion means 22. Partition layer 24, in a presently preferred embodiment, comprises a composition that is substantially impermeable to the passage of fluid, and it serves to restrict the passage of fluid present in the expansion means into that area of compartment 18 that contains the agent formulation. It operates to essentially maintain the integrity of the active agent formulation and the expansion means layer. Additionally, and importantly, partition layer 24 acts to insure that the expanding driving force generated by the expansion means 22 is applied directly against the first wall section 14 to effect the separation of the two wall sections. Thus, partition layer 24 must be of sufficient strength, thickness and rigidity to transfer the driving force against first wall section 14.

First wall section 14 has an open end with a recessed outer edge for forming receiving means 26 for slidably receiving and engaging the open end of second wall section 16. The two wall sections at their open ends are close in size and they form a friction fit therebetween. The friction generated is sufficient to maintain the two wall sections together prior to activation of the expansion means but not so great as to keep the two wall sections from sliding apart once an expanding driving force is exerted. First wall section 14 and second wall section 16 can be telescoped completely into a closed and continuous external walled position. The open end of first wall section 14 is adapted to fit within second wall section 16. The bottom edge of the open end of first wall section 14 provides a platform or ridge 28 protruding into compartment 18. Ridge 28 is adapted to receive the driving force of the expansion means 22, via the partition layer 24, to effect the separation of the two wall sections.

In operation, as the expansion means 22 absorbs and imbibes fluid through second wall section 16 from the environment of use, it expands and pushes against partition layer 24, causing the partition layer to slide inside compartment 18. Partition layer 24 moves toward and contacts ridge 28, pushing against ridge 28 and thus against first wall section 14 to cause the first wall section to slide apart from second wall section 16 as the expansion means 22 continues to expand. This causes the two wall sections to become separated and the active agent formulations 20 to be exposed to the environment of use, as illustrated in FIG. 2.

Figure 2:
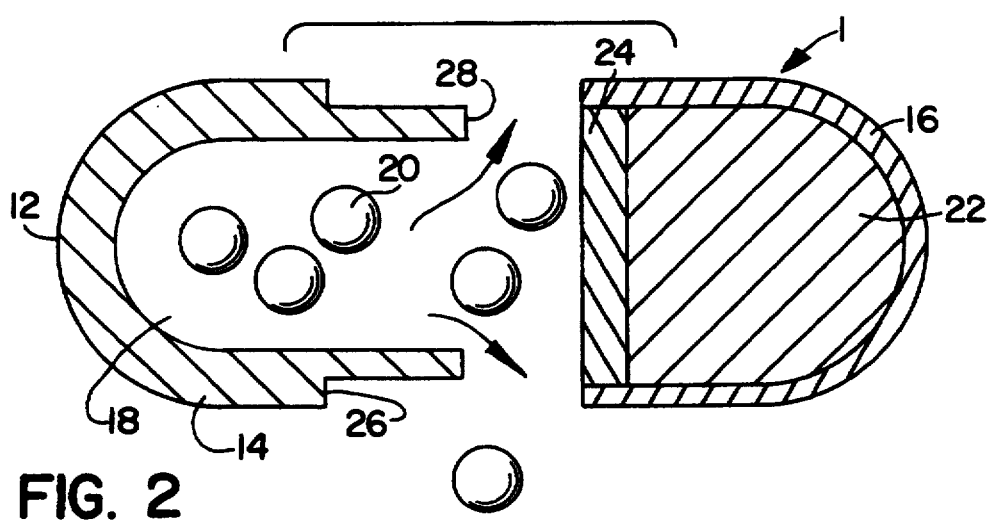
FIG. 2 is the device of FIG. 1 in operation after activation by placement in the environment of use, showing the device opened to release the active agent formulation to the environment.

FIG. 2 illustrates the dispensing device 1 of FIG. 1 in operation after activation of the device by placement in the environment of use. FIG. 2 shows device 1 opened to release all of the active agent dosage forms 20 to the environment substantially at the same time. First wall section 14 has been separated from second wall section 16 by the expanding driving force of the expansion means 22, which has expanded in size as a result of imbibing fluid from the environment. The arrows in FIG. 2 indicate the exiting of the agent formulation dosage forms 20 from internal compartment 18 through the open end of first wall section 14, which is now in communication with the environment.

First wall section 14 may comprise a composition that is semipermeable, that is, it is permeable to fluid but impermeable to active agent and other ingredients contained in dispensing device 1, or it may, alternatively, comprise a composition that is impermeable to the exchange of fluid, agent and other ingredients. When an active agent or an active agent dosage form is sensitive to fluid from an exterior fluid present in the environment of use, it is preferred that first wall section 14 be substantially impermeable to the ingress of the external fluid to serve as a means for substantially protecting the agent or dosage form.

Because expansion means 22 operates by the inhibition of external fluid, second wall section 16 in at least a portion that is adjacent to expansion means 22 must be permeable or semipermeable; that is, it is permeable to the passage of fluid while being substantially impermeable to the passage of other ingredients contained in dispensing device 1.

Wall sections 14 and 16 optionally comprise additional ingredients such as, for example, a plasticizer. Impermeable and semipermeable compositions suitable for use in wall sections 14 or 16, as well as suitable additives, are known in the art, examples of which are disclosed in U.S. Pat. 4,874,388, the entire disclosure of which is incorporated herein by reference.

Housing 12, comprising wall sections 14 and 16, is nontoxic, biologically inert, nonallergenic and nonirritating to body tissue, and it maintains its physical and chemical integrity; that is, housing 12 does not erode or degrade in the environment of use during the dispensing period. It is within the scope of the invention that the housing be insoluble only during the period of intended use and can thereafter dissolve away in the environment of the device. Thus, a dispenser is here contemplated which is unaffected by its environment, solubility wise, at the situs of use or which, alternatively, is only slightly soluble during the period of intended use, such that once its active agent content has been removed it will then dissolve or erode away leaving no objectionable residue or empty container at the situs of use.

The expansion means or expandable driving means 22, operable for separating the first and second wall sections to release the active agent from the dispensing device of the invention, is nontoxic, nonallergenic and biologically inert. Expansion means 22 comprises, in one presently preferred embodiment, an osmopolymer. The osmopolymers interact with water and aqueous biological fluids and swell or expand to an equilibrium state. The osmopolymers exhibit the ability to swell in fluid and to retain a significant portion of the imbibed and absorbed fluid within the polymer structure. The expansion means 22 in another preferred embodiment comprises an osmagent. The osmagents are known also as osmotically effective solutes and they are also known as osmtocially effective compounds. The osmagents that can be used for the purpose of this invention include inorganic and organic compounds that exhibit an osmotic pressure gradient across a semipermeable, i.e. a fluid-permeable, wall. The expansion means 22 in yet another preferred embodiment comprises an osmagent dispersed within an osmopolymer. The expansion means 22 can comprise a tablet or a layer, or a plurality of tablets or layers, or it can be pressed into second wall section 16. The osmagent or osmopolymer can be in any suitable form such as particles, crystals, pellets, granules, and the like, when pressed into a tablet layer and into wall section 16. The means for expanding and separating the respective member comprises 10 ng to 10 g of the operative composition. Osmagents and osmopolymers are known to the art and are described in, for example, U.S. Pat. Nos. 3,865,108, 4,002,173, 4,207,893, 4,327,725 and 4,612,008.

Partition layer 24, present in certain embodiments of the invention between the active agent formulation and the expansion means, is a means for transmitting the force generated by the expansion means against the first wall section 14, for maintaining the separate identity of the active agent formulation and the expansion means, and for substantially restricting the passage of fluid between the active agent formulation and the expansion means. Representative materials useful as a partition layer 24 are known to the art in, for example, U.S. Pat. No. 4,874,388.

The term "active agent formulation", as used herein, comprises the active agent to be delivered, as a liquid, solid, semisolid or thermosensitive composition, generally in a carrier substance and with or without additional inert ingredients. The term may additionally include dosage forms comprising the active agent which are capable of maintaining their physical configuration and chemical integrity while housed within the dispenser. These include, without limitation, tablets with or without a density element; matrix tablets; spheres; tiny pills; pellets and elongated tablets; capsules; elementary osmotic pumps, such as those described in U.S. Pat. No. 3,845,770; mini-osmotic pumps, such as those described in U.S. Pat. Nos. 3,995,631, 4,034,756 and 4,111,202; and multichamber osmotic systems referred to as push-pull and push-melt osmotic pumps, such as those described in U.S. Pat. Nos. 4,320,759 and 4,449,983; all the above patents of which are incorporated herein by reference.

The pharmaceutically acceptable carrier useful herein may comprise more than one ingredient, such as, for example, a buffer, a viscosity regulating vehicle, a surfactant, dyes, a permeation enhancer, proteinase inhibitors, or other formulation ingredients and additives, as are known in the art. The carrier may contain more than one active agent. The active agent formulation can erode or disintegrate and can be in the form of a wax formulation, solid core or tablet, for example. The formulation can immediately dissolve upon exposure to fluid or it may erode slowly with or without the presence of excipients for controlling erosion.

The active agent formulation can be designed in a multitude of ways to provide a specific drug delivery profile. One embodiment may comprise a formulation that contains a biologically acceptable solid surfactant which is capable of slow dispersion in the environmental fluid. In another embodiment, the formulation may contain a fluid-insoluble wax and a surfactant so that the formulation is susceptible to erosion in the environment. In still another embodiment, the formulation may be effervescent and provide drug delivery in a finely dispersed form. This is accomplished by the addition of a solid basic compound capable of evolving carbon dioxide in the presence of an acid in the environment of use. Suitable basic compounds are disclosed in U.S. Pat. No. 4,265,874. In a further embodiment, the formulation may include an osmotic agent or solute, such as those described above with reference to the expansion means 22, so that when the formulation comes into contact with the environmental fluid, it immediately dissolves. In yet another embodiment, the agent formulation can be comprised of an agent and a thermo-responsive composition. In this manner, the formulation would exhibit solid-like properties at room temperature of 21° C. and within a few degrees Celsius thereof, and would have a melting point that approximates mammalian body temperatures of 37° C. and within a few degrees Celsius thereof. The term "thermoresponsive" as used herein in a preferred embodiment denotes the physical-chemical property of an agent carrier composition to exhibit solid, or solid-like properties at temperatures up to 31° C. and become fluid, semi-solid or viscous when disturbed by heat at temperatures from 31° C., usually in the range of 31° C. to 45° C. Suitable materials useful as active agent carriers and excipients are known in the art and are disclosed in U.S. Pat. Nos. 4,595,583 and 4,874,388, for example.

The terms "active agent" and "drug" are used interchangeably herein and refer to an agent, drug, compound, composition of matter or mixture thereof which provides some therapeutic, often beneficial, effect. This includes pesticides, herbicides, germicides, biocides, algicides, rodenticides, fungicides, insecticides, antioxidants, plant growth promoters, plant growth inhibitors, preservatives, antipreservatives, disinfectants, sterilization agents, catalysts, chemical reactants, fermentation agents, foods, food supplements, nutrients, cosmetics, drugs, vitamins, sex sterilants, fertility inhibitors, fertility promoters, microorganism attenuators and other agents that benefit the environment of use. As used herein, the terms further include any physiologically or pharmacologically active substance that produces a localized or systemic effect or effects in animals, including warm blooded mammals, humans and primates; avians; domestic household or farm animals such as cats, dogs, sheep, goats, cattle, horses and pigs; laboratory animals such as mice, rats and guinea pigs; fish; reptiles; zoo and wild animals; and the like. The active drug that can be delivered includes inorganic and organic compounds, including, without limitation, drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autocoid systems, the alimentary and excretory systems, the histamine system and the central nervous system. Suitable agents may be selected from, for example, proteins, enzymes, hormones, polynucleotides, nucleoproteins, polysaccharides, glycoproteins, M. lipoproteins, polypeptides, steroids, hypnotics and sedatives, psychic energizers, tranquilizers, anticonvulsants, muscle relaxants, antiparkinson agents, analgesics, anti-inflammatories, local anesthetics, muscle contractants, antimicrobials, antimalarials, hormonal agents including contraceptives, sympathomimetrics, polypeptides and proteins capable of eliciting physiological effects, diuretics, lipid regulating agents, antiandrogenic agents, antiparasitics, neoplastics, antineoplastics, hypoglycemics, nutritional agents and supplements, growth supplements, fats, ophthalmics, antienteritis agents, electrolytes and diagnostic agents.

Examples of beneficial agents which this invention can be utilized with are prochlorperazine edisylate, ferrous sulfate, aminocaproic acid, mecaxylamine hydrochloride, procainamide hydrochloride, amphetamine sulfate, methamphetamine hydrochloride, benzphetamine hydrochloride, isoproteronol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, mecl izine hydrochloride, prochlorperazine maleate, phenoxybenzamine, thiethylperazine maleate, anisindone, diphenadione erythrityl tetranitrate, digoxin, isoflurophate, acetazolamide, methazolamide, bendroflumethiazide, chlorpropamide, tolazamide, chlormadinone acetate, phenaglycodol, allopurinol, aluminum aspirin, methotrexate, acetyl sulfisoxazole, erythromycin, hydrocortisone, hydrocorticosterone acetate, cortisone acetate, dexamethasone and its derivative; such as betamethasone, triamcinolone, methyltestosterone, 17-$\beta$-estradiol, ethinyl estradiol, ethinyl estradiol 3-methyl ether, pednisolone, 17-$\beta$-hydroxyprogesterone acetate, 19-norprogesterone, norgestrel, norethindrone, norethisterone, norethiederone, progesterone, norgesterone, norethynodrel, aspirin, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chlorpromazine, methyldopa, dihydroxyphenyl alanine, theophylline, calcium gluconate, ketoprofen, ibuprofen, cephalexin, erythromycin, haloperidol, zomepirac, ferrous lactate, vincamine, diazepam, phenoxybenzamine, diltiazem, milrinone, captropril, mandol, quanbenz, hydrochlorothiazide, ranitidine, flurbiprofen, fenbufen, fluprofen, tolmetin, alclofenac, mefenamic, flufenamic, difuninal, nimodipine, nitrendipine, nisoldipine, nicardipine, felodipine, lidoflazine, tiapamil, gallopamil, amlodipine, mioflazine, lisinopril, enalapril, captopril, ramipril, endlapriat, famotidine, nizatidine, sucralfate, etintidine, tetratolol, minoxidil, chlordiazepoxide, diazepam, amitriptylin, and imipramine. Further examples are proteins and peptides which include, but are not limited to, insulin, colchicine, glucagon, thyroid stimulating hormone, parathyroid and pituitary hormones, calcitonin, renin, prolactin, corticotrophin, thyrotropic hoemone, follicle stimulating hormone, choriOnic gonadotropin; gonadotropin releasing hormone, bovine somatotropin, porcine somatropin, oxytocin, vasopressin, prolactin, somatostatin, lypressin, pancreozymin, luteinizing hormone, LHRH, interferons, interleukins, growth hormones such as human growth hormone, bovine growth hormone and porcine growth hormone, fertility inhibitors such as the prostaglandins, fertility promoters, growth factors, and human pancreas hormone releasing factor.

It is to be understood that more than one active agent may be incorporated into the active agent formulation in a device of this invention, and that the use of the term "agent" or "drug" in no way excludes the use of two or more such agents or drugs.

The agents can be in a wide variety of chemical and physical forms, such as uncharged molecules, components of molecular complexes or nonirritating, pharmacologically acceptable salts. Also, simple derivatives of the agents (such as ethers, esters, amides, etc.) which are easily hydrolyzed by body pH, enzymes, etc., can be employed.

The amount of active agent employed in the delivery device will be that amount necessary to deliver a therapeutically effective amount of the agent to achieve the desired result at the site of delivery. In practice, this will vary widely depending upon the particular agent, the site of delivery, the severity of the condition, and the desired therapeutic effect. Thus, it is not practical to define a particular range for the therapeutically effective amount of active agent incorporated into the device; however, for the present purpose, the device will comprise 10 ng to 10 g of a therapeutic agent.

Figure 3:
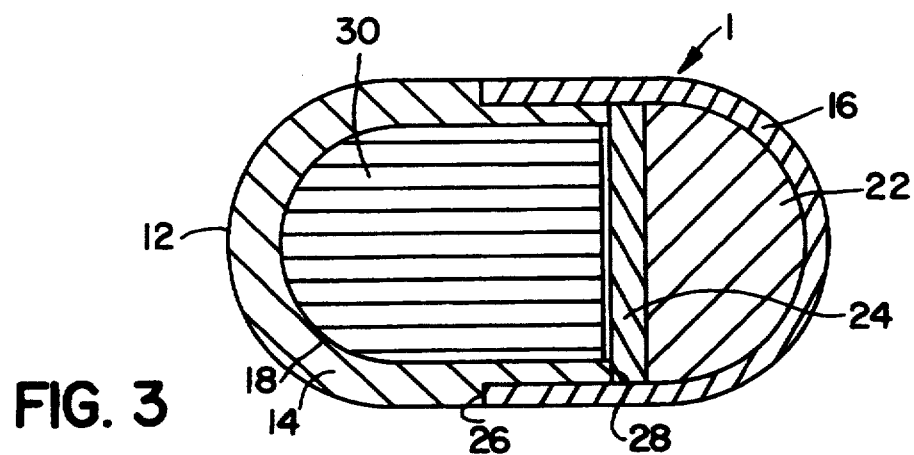
FIG. 3 is a cross-sectional view of the device of FIG. 1 but containing a different form of an active agent formulation.

FIG. 3 illustrates another embodiment of the dispensing device 1 of the present invention. As illustrated in this figure, dispensing device 1 is similar to the dispensing device of FIGS. 1 and 2, having a housing 12, a first wall section 14, a second wall section 16, an internal compartment 18 surrounded and defined by housing 12, expansion means 22, partition layer 24, receiving means 26 and ridge 28, but contains an active agent formulation 30 that is of a different form than that of FIGS. 1 and 2. Active agent formulation 30 is present as a single homogeneous or heterogeneous mass and may be in solid, liquid or semi-solid form or may comprise a thermosensitive composition. Agent formulation 30 may comprise a pharmaceutically acceptable carrier in addition to the active agent, with the agent being dispersed homogeneously or heterogeneously within the carrier.

FIG. 4 illustrates another embodiment of the dispensing device of the present invention. Dispensing device 2 comprises a housing 12 formed of a first wall section 14 and a second wall section 16. First wall section 14 and second wall section 16 are in slidably telescoping arrangement with each other. Housing 12 surrounds and defines an internal compartment 18. Internal compartment 18 contains an active agent formulation, in this embodiment the formulation being a plurality of active agent dosage forms 20. Alternatively, the active agent formulation could be present as solid, semi-solid or liquid particles of active agent formulation dispersed in compartment 18. Internal compartment 18 also contains an expansion means 22 within a portion and, preferably, within substantially all of compartment 18 for expanding and for occupying space in the compartment. The active agent formulation may be dispersed throughout the expansion means 22 within compartment 18. At least one, and preferably both of first wall section 14 and second wall section 16 are comprised in at least a portion of a semipermeable composition so that fluid may be imbibed into the compartment to activate expansion means 22. As expansion means 22 takes up fluid and expands, a high internal pressure is created and the resulting driving force is exerted against the closed ends of the wall sections 14 and 16, causing the open ends of the two wall sections, which are held together by a friction fit therebetween, to slide apart and become separated, releasing active agent dosage forms 20 into the environment of use.

A multi-pulse delivery of active agent formulation over an extended period of time, such as 24 hours, may be provided by utilizing sequentially smaller dispensing devices of the invention enclosed within each other. Such a multi-pulse dispenser is illustrated in FIG. 5. In FIG. 5, multi-pulse dispensing device 3 is comprised of a plurality of housings 12a, 12b and 12c, each smaller than the other and contained within the internal compartment of the next larger housing. Thus, housing 12c is contained within internal compartment 18b of housing 12b, and housing 12b (containing housing 12c) is itself contained within internal compartment 18a of housing 12a. Also contained within each of the compartments 18a, 18b and 18c are active agent formulation dosage forms 20a, 20b and 20c, respectively, dispersed in expansion means 22a, 22b and 22c, respectively. As housing 12a is opened by the expanding driving force of expansion means 22a, it releases housing 12b into the environment of use as it releases active agent dosage forms 20a. Housing 12b is then exposed to the environmental fluid and is opened after a delay period by the expanding driving force of expansion means 22b, releasing active agent dosage forms 20b together with housing 12c. Housing 12c in its turn is then exposed to the environmental fluid to release active agent dosage forms 20c by expansion of means 22c.

FIG. 6 illustrates an embodiment of the invention where two active agents are delivered from the same device. Such a dispensing device is desirable when, for example, the agents must be kept separated because they are physically or chemically incompatible with each other or when the agents are to be delivered to the environment at different points in time. Dispensing device 4 comprises a housing 12 formed of a first wall section 14 and two second wall sections 16a and 16b. First wall section 14 has two opposing open ends and includes an impermeable internal dividing wall 17 which divides the space encompassed by housing 12 into two internal compartments 18a and 18b. That part of first wall section 14 encompassed by one of its two open ends and dividing wall 17 surrounds that portion of internal compartment 18a that contains an active agent formulation 30a. That part of first wall section 14 encompassed by the other of its two open ends and dividing wall 17 surrounds that portion of internal compartment 18b that contains an active agent formulation 30b. Formulations 30a and 30b may comprise the same active agent or different active agents. The two formulations may be the same or different; for example, they may both be liquids, or one may be solid and one liquid, or one may be a liquid and the other a plurality of dosage forms. Formulations 30a and 30b may comprise the same active agent but in two different chemical forms, such as the base drug and a salt of the same drug.

Second wall section 16a of dispensing device 4 surrounds that portion of internal compartment 18a that contains an expansion means 22a for expanding and for occupying space in compartment 18a. Second wall section 16a also contains a partition layer 24a, which layer 24a is positioned between the agent formulation 30a and the expansion means 22a. Second wall section 16b surrounds that portion of internal compartment 18b that contains an expansion means 22b for expanding and for occupying space in compartment 18b. Second wall section 16b also contains a partition layer 24b, which layer 24b is positioned between the agent formulation 30b and the expansion means 22b. The bottom edge of each of the open ends of first wall section 14 provides a platform or ridge 28a and 28b protruding into compartments 18a and 18b, respectively, for receiving the driving force of the expansion means via partition layers 24a and 24b, respectively, to separate apart the first wall section and the second wall sections.

Where it is desired to deliver active agent formulations 30a and 30b substantially concurrently, the composition of expansion means 22a and 22b will be the same so that they will have identical expansion profiles, to separate the first wall section from both second wall sections at substantially the same time. Where it is desired, on the other hand, to deliver active agent formulations 30a and 30b at different points in time, that is, after different initial delay periods (a multi-pulse system), the composition of the two expansion means will be different in order to provide the different initial delay periods.

Another embodiment of the invention is very similar to that illustrated in FIG. 6 except that it does not include an impermeable internal dividing wall 17. Thus, the delivery device of this similar embodiment comprises a housing 12 formed of a first wall section 14 and two second wall sections 16a and 16b, expansion means 22a and 22b, partition layers 24a and 24b, and ridges 28a and 28b. First wall section 14 has two opposing open ends and encompasses one internal compartment 18, which compartment 18 contains one active agent formulation 30 or a plurality of dosage forms 20. This double-capped embodiment is useful when it is desired to expedite the release of the active agent formulation 30 or 20 from the device once the agent formulation is exposed to the environment of use. In such a use, the composition of expansion means 22a and 22b will normally be the same so that the expansion means will separate the first wall section from the two second wall sections at substantially the same time to release the active agent formulation 30 or 20.

It may, in certain instances, be desirable to provide an initial rapid delivery of an active agent to the environment of use in addition to the delayed delivery of active agent provided by this invention. Such initial agent delivery may be accomplished by means for providing an initial agent dose. FIG. 7 illustrates one means of initial agent delivery. In FIG. 7, dispensing device 5 comprises housing 12 having a first wall section 14 and a second wall section 16, internal compartment 18, active agent formulation dosage forms 20, expansion means 22, partition layer 24, receiving means 26 and ridge 28. Dispensing device 5 additionally comprises an initial agent delivery means or loading dose 32. Loading dose 32 comprises at least one active agent homogeneously or heterogeneously dispersed or dissolved in an appropriate carrier means, which can be a solid, paste, gel, semisolid, or the like, or a thermosensitive material which provides a dispensable material in the environment of use. The loading dose 32 can be in the form of a tablet or capsule, for example, and can be round, spheroid, toroid, cylindrical, square, and the like. Loading dose 32 is located on or within dispensing device 5 in such a manner that, upon application of the device to the environment of use, the loading dose is immediately exposed to the environment. This may be accomplished by means of a retaining device such as a ridge (as illustrated by retaining ridge 46) or a screen, for example. Once device 5 is placed in the environment of use, loading dose 32 dissolves, erodes, osmotically bursts or otherwise begins to dispense the active agent contained therein. At the same time, expansion means 22 will begin to imbibe fluid, expanding to begin to separate first wall section 14 and second wall section 16. This provides a pulsed delivery of agent from loading dose 32 at a first time period and of agent from the agent dosage forms 20 at a second time period. The formulation of the loading dose 32 can be so designed that the delivery of the initial agent could be completed prior to the delivery of the dosage forms 20 or, alternatively, that the initial agent could provide a continuous delivery for a period up to and even after the delivery of the dosage forms. The loading dose and the agent dosage forms may contain the same active agent or different active agents.

Delivery of an initial agent dose may also be accomplished by coating housing 12 externally with an overcoat or loading dose containing an active agent. Once placed in the environment of use, the loading dose overcoat will begin immediately to dissolve, erode or otherwise dispense an active agent contained in the loading dose. In this embodiment, the expansion means of the device cannot begin to imbibe water and become activated until such time as the loading dose overcoat has dissolved or eroded away from the semipermeable membrane of second wall section 16, so that a good portion if not all of the active agent in the loading dose will have been dispersed prior to the dispersion of the agent in active agent formulation 20 or 30 from the device, thus providing a multi-pulse delivery of agent.

FIGS. 8 and 9 are cross-sectional views of another preferred embodiment of the dispensing device of the present invention, prior to delivery (FIG. 8) and subsequent to delivery (FIG. 9) of the device to an environment of use. Dispensing device 6 comprises a housing 12 formed by a first wall section 14 and a second wall section 16, the two wall sections being in slidably telescoping arrangement and enclosing an internal compartment 18. That portion of compartment 18 enclosed by first wall section 14 contains a first expansion means 34 and a first active agent formulation 36, which in a preferred embodiment are separated by a moveable impermeable first partition layer 38 to maintain the separate identities of the first agent formulation 36 and the first expansion means 34. It also contains a second active agent formulation 30 and an impermeable barrier layer 40 which separates first expansion means 34 from second active agent formulation 30. Barrier layer 40 is preferably nonmoveable in the device. First wall section 14 also comprises an exit means or port 42 which provides communication between the environment of use and that part of internal compartment 18 containing first active agent formulation 36.

The terms "exit means", "exit port" and "exit passageway", as used herein, comprise means and methods suitable for the metered release of the active agent formulation from compartment 18 of the delivery device of the present invention. The exit means 42 includes at least one passageway, orifice, or the like, through first wall section 14 for communicating with compartment 18. The expression "at least one passageway" includes aperture, orifice, bore, pore, porous element through which the agent can migrate, hollow fiber, capillary tube, porous overlay, porous insert, and the like. The expression also includes material that is discharged, erodes or is leached from the wall in the fluid environment of use to produce at least one passageway in the delivery device. Representative materials suitable for forming at least one passageway, or a multiplicity of passageways, include an erodible poly(glycolic) acid or poly(lactic) acid member in the wall; a gelatinous filament; poly(vinyl alcohol); leachable materials such as fluid-removable pore-forming polysaccharides, salts, or oxides; erodable or dischargable materials such as natural and synthetic waxes; and the like. The expression includes structural characteristics that concentrate stress at a precise point in the wall so that only a small amount of force will induce breakage in the wall, yielding a passageway through the wall from compartment 18 to the outside of the device. A passageway or a plurality of passageways can be formed by leaching a material such as sorbitol, lactose and like water-soluble solids from the wall. A passageway or passageways can be formed by the discharge, as a result of the pressure created by the expandable driving means for example, of a material such as a wax. The exit means or passageway can have any shape such as round, triangular, square, elliptical, and the like, for assisting in the metered release of active agent from the delivery device. The delivery device can be constructed with one or more passageways in spaced-apart relations or more than a single surface of a dosage form. Passageways and equipment for forming passageways are disclosed in U.S. Pat. Nos. 3,845,770; 3,916,899; 4,063,064; and 4,088,864. Passageways formed by leaching are disclosed in U.S. Pat. Nos. 4,200,098 and 4,285,987.

That portion of compartment 18 enclosed by second wall section 16 contains a second expansion means 22 and a moveable impermeable second partition layer or push plate 24, the second partition layer or push plate 24 being between second expansion means 22 and second active agent formulation 30 and positioned to come into contact with the end or ridge 28 of the open end of first wall section 14.

At least that portion of first wall section 14 adjacent to first expansion means 34 must be of a semipermeable composition, since the expansion means is activated by the imbibition of water. Likewise, second wall section 16 is of semipermeable composition. When first wall section 14 is semipermeable adjacent to second active agent formulation 30, an impermeable inner wall 44 may be present between first wall section 14 and agent formulation 30 when it is desired to protect the active agent in formulation 30 from fluid from the environment. Such an additional impermeable wall may also be present between wall section 14 and first active agent formulation 36 when it is desired to protect the active agent in formulation 36 from fluid from the environment.

In practice, as fluid is imbibed by first expansion means 34, the expanding driving force of means 34 is conveyed via first partition layer 38 against the first active agent formulation 36, and agent formulation 36 is then immediately begun to be expelled in a controlled and prolonged manner from internal compartment 18 through exit port 42 into the environment of use, providing an initial active agent dose. At the same time, second expansion means 22 begins to expand and exert a driving force via second partition layer or push plate 24 against end or ridge 28 of first wall section 14 to begin to slidably separate first wall section 14 from second wall section 16. Second agent formulation 30 is only delivered to the environment of use at the point in time ($t_b$) when first wall section 14 and second wall section 16 have separated apart from each other. In such a manner, first agent formulation 36 is continuously delivered to the environment for an extended or prolonged time ($t_a$) while a pulse of second agent formulation 30 is delivered at a later, delayed time ($t_b$). First agent formulation 36 and second agent formulation 30 may comprise the same active agent or different active agents or they may comprise the same active agent in different forms.

Figure 8:
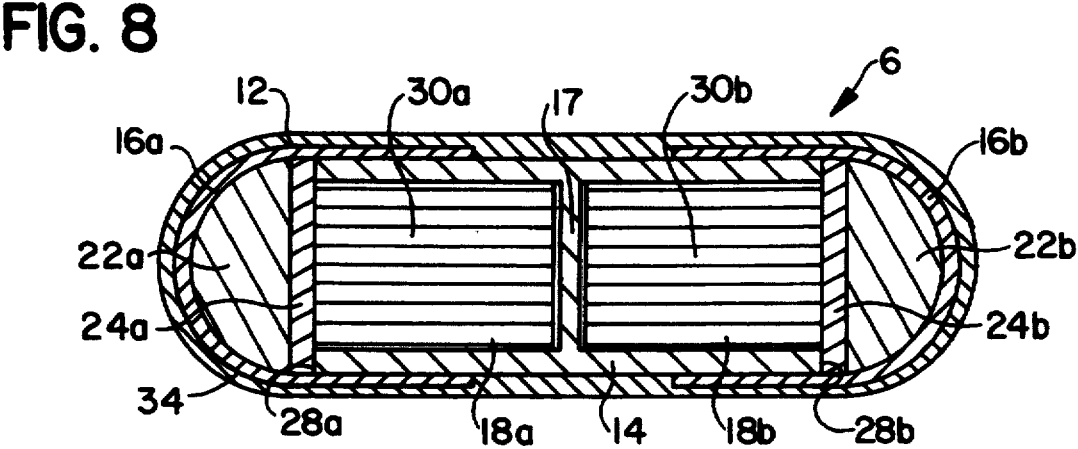
FIG. 8 is a cross-sectional view of a further embodiment of the present invention where one active agent is to be delivered in a controlled manner over a prolonged period of time and a second active agent is to be delivered after an initial delay period, the device being in closed form prior to placement in the environment of use.

FIG. 10 illustrates another embodiment of the device of the invention. As illustrated in this figure, dispensing device 7 is similar to dispensing device 6 of FIGS. 8 and 9, having a housing 12, a first wall section 14 with a ridge 28, a second wall section 16, an internal compartment 18 surrounded and defined by housing 12, first expansion means 34, second expansion means 22, first partition layer 38, second partition layer or push plate 24, barrier layer 40, and exit means 42. In dispensing device 7, the second active agent formulation is present as a plurality of active agent dosage forms as tiny pills 20 and the first active agent formulation is present as a plurality of active agent dosage forms as layers or tablets 52, 54, 56 and 58. Although four dosage layers are illustrated, the number is not critical and any number of dosage layers are included under the invention. Optionally, layers of a barrier material (not shown) may be placed between the agent dosage layers in alternating arrangement to provide a prolonged, repeating pulsed delivery. The exit means or passageway 42 may optionally be closed by an erodible material 60 such as, for example, microcrystalline wax or gelatin, for protecting the first active agent formulation prior to placement in the fluid environment, or there may optionally be present a retaining structure such as a screen or mesh for retaining the dosage layers within the device until they are dispensed into the environment.

Figure 11:
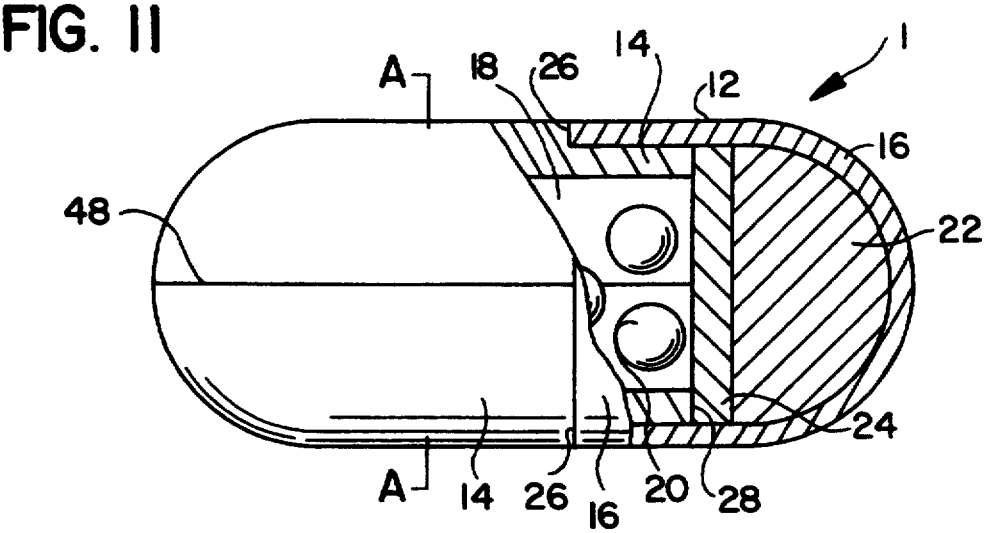
FIG. 11 is a partial cross-sectional view of another embodiment of the invention, having a first wall section of two longitudinal halves.

FIG. 11 illustrates, in partial cross-sectional view, a device 1 similar to the devices described in FIGS. 1–3 and having a housing 12 comprised of first wall section 14 and second wall section 16, an internal compartment 18 surrounded and defined by housing 12, a plurality of dosage forms 20, expansion means 22, partition layer 24, receiving means 26 and ridge 28. FIG. 11 illustrates an alternative embodiment of the present invention where the first wall section 14 is comprised of two longitudinal halves which contact each other at longitudinal junction 48. It is to be noted that, while two longitudinal portions are presented by way of illustration, the invention is not limited thereto, and second wall section 14 may be comprised of from one to four or more longitudinal portions. The two longitudinal halves are held together by the pressure exerted on them by that portion of the open end of second wall section 16 that overlaps the open end of first wall section 14. When the two wall sections are separated by the action of the expansion means 22, the two longitudinal halves of first wall section 14 become free of the restraining pressure of second wall section 16 so that the two longitudinal halves can then separate from each other to provide additional exposure of active agent formulation to, or to aid in the release of the active agent formulation to the environment of use.

The device of this invention, in one manufacture comprise a wall that surrounds and defines an internal space. The wall, in one embodiment, comprises a first section and a second section, with each section composed of a closed end and an opened end. The opened ends, when in contacting mated relation form a closed housing for containing compositional and operative components. The device embraced by this general structure can comprise a capsule-shaped device. The term capsule is generic for the purpose of this invention and it comprises a plurality of structurally different capsules.

The device capsule comprises two parts composed of a cap and a body that fit together in closed relation. The device capsule comprises shapes and sizes including oblong-shaped, cylinderical-tubular shaped, spherical-shaped, spheroidal-shaped, elliptical-shaped, oval-shaped and conventional capsule-shaped forms. The capsules comprise sizes of (000), (00), (0), (1), (2), (3), (4) and (5), with a diameter of 1.5 mm to 15 mm, as defined by the Pharmacopoeia in *Microcapsule Processing and Technology*, by Kondo and Van Valkenburg, Chapter 2, page 1, (1979), published by Marcel Dekker, Inc.

The dosage capsule comprises a multiplicity of manufactures, for example, a cylinderical-tubular shaped capsule composed of a top and bottom cylinder having rounded or flat ends and feature a tight friction therebetween, with clearance or tolerance in the sizes to allow a sliding movement between the cylinders; an elliptical capsule comprising a wall that defines and forms a cavity composed of a head and body having approximately equal external diameter at the point of junction of the head and body; a capsule of polygonal, hexagonal or round cross-section with inter-locking and releasable engaging portions on the cap and body sections; a capsule united by engaging a circumferential slot on a body section for engaging a raised surface member on a cap section to provide a capsule having a body and cap in alignment indicated for oral use; a capsule composed of a first and second sections detachably joined in a co-linear arrangement by an annular band at the point of contact of the sections; a capsule composed of two sections attachable together by complimentary frictionally-engaging surfaces with the inner surfaces of one section impacted against the outer surface of the other section; a capsule of generic shaped composed of a coaxial body and cap which cap overlaps the body to provide a closed capsule; a capsule composed of a hexagonal wall with body and cap portions and open ends which are telescopically engaged to provide a closed capsule; and a capsule composed of cylindrical telescopically joinable coaxial cap and body each having a side wall and opened end and closed end with the cap and body adapted to be mutually joined with the body enclosed with the cap.

A device capsule can be made in another manufacture by dipping stainless steel molds in a bath containing a solution of a capsule-forming composition. The molds are withdrawn, cooled and dried in a current of air. The capsule is stripped from the mold and trimmed to yield the capsule member comprising its internal lumen. The engaging cap that telescopically caps the formulation receiving body is made in a similar manner.

Figure 12A:
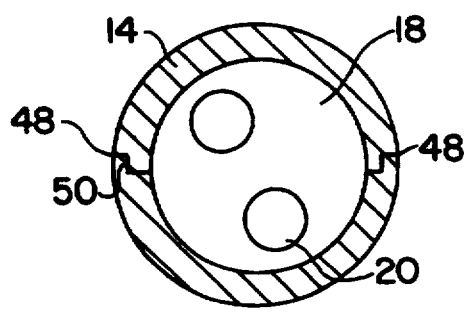
FIGS. 12a and 12b are views through the first wall section of the embodiment of FIG. 11 along line A—A.
Figure 12B:
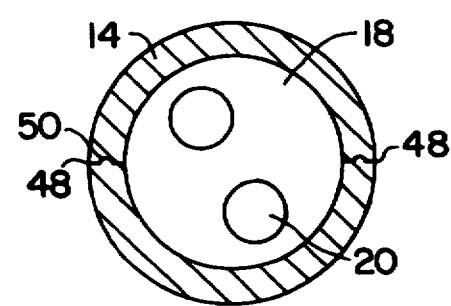

As illustrated in FIGS. 12a and 12b, which are section views along line A—A of device 1 of FIG. 11, the longitudinal walls of the two halves of first wall section 14 may be so shaped as to provide an interlocking means 50 between the two halves at the longitudinal junction 48. The interlocking means 50 may be, for example, an interlocking ridge that runs continuously along the length of the longitudinal walls of the two halves (FIG. 12a) or a plurality of interlocking concave and convex structures positioned at corresponding points along the longitudinal walls of the two halves (FIG. 12b). The interlocking means 50 provides an additional mechanism for maintaining the two longitudinal halves together while the device 1 is in closed form.

For proper delivery of the active agent, it may be desirable in some instances for the dispensing device to deliver active agent to a particular environment of use. Thus, it may be necessary for the device to remain in a particular environment of use until such time as the agent formulation has been delivered or, alternatively, for the device to pass through one particular environment to another prior to delivering agent formulation. In such cases, additional elements are included in the device, or the device is designed in such a way to provide for such particular delivery. For example, when the environment of use is the rumen of a ruminant animal, a density element may be included in the dispensing device so that the device is weighted to remain within the rumen during the dispensing period. Density elements are known in the art and are discussed in, for example, U.S. Pat. No. 4,874,388. When the environment of use is the human stomach, it may be desirable for the device to, for example, have a low initial density or to include air in that portion of the internal compartment of the device that also contains the agent formulation. In this manner, the device will float on the surface of the stomach contents and remain in the stomach until the device opens to release the formulation. Where it is desirable, on the other hand, to delay the release of an active agent which, for example, is inactivated by the stomach contents or may cause nausea or bleeding by irritating the gastric mucosa so that delivery in the stomach is not desired, an enteric coating can be applied over at least that portion of the housing of the dispensing device that is comprised of a semipermeable membrane. Enteric coatings will remain intact in the stomach but will rapidly dissolve once they arrive at the small intestine, thereafter allowing fluid to be imbibed to activate the dispensing device. Enteric coatings are well known in the art and are discussed at, for example, "Remington's Pharmaceutical Sciences", Mack Publishing Co., Easton, PA.

The total delay time prior to separation of the dispensing device and delivery of the active agent formulation can be controlled by a number of means. For example, the rate of fluid imbibition into the expansion means can be controlled by the particular choice of semipermeable membrane. The rate of expansion of the expansion means can be controlled by the choice of composition of the expansion means. The distance of overlap between the open end portions of the first and second wall sections can determine the period of time required for the two sections to separate. Combinations of such means may be used. Such control means are known in the art and can be determined without undue experimentation.

The above description has been given for ease of understanding only. No unnecessary limitations should be understood therefrom, as modifications will be obvious to those skilled in the art.

The following examples are illustrative of the present invention. They are not to be construed as limitations of the scope of the invention. Variations and equivalents of these examples will be apparent to one skilled in the art in light of the present disclosure, the drawings and the claims herein.

EXAMPLE 1

A delivery device according to the invention was prepared as follows.

The osmotic engine portion of the device is a compressed bilayer tablet composed of a 150 mg polymeric osmotic formulation (expansion means) and a 50 mg wax-based barrier.

The polymeric osmotic formulation has a composition of 60 wt % polyethylene oxide (Polyox®303, Union Carbide), 29 wt % sodium chloride, 5 wt % polyacrylic acid (Carbomer®934P, B.F. Goodrich), 5 wt % hydroxypropylmethylcellulose E-5, and 1 wt % ferric oxide. During preparation, each of the above components was screened through a 40 mesh screen, and the sized components were added to a mixing vessel in the appropriate proportions. The dry components were mixed thoroughly for 10 minutes; then, SDA 3A ethanol was slowly added while mixing continued until a wet mass had formed. The wet mass was then screened through a 20 mesh screen, and the wet granules were allowed to air dry for 18 hours. After drying, the granules were passed once more through a 20 mesh screen.

The wax barrier has a composition of 95 wt % microcrystalline wax (MF-2JH Durawax®, Astor Wax Corp.) and 5 wt % gelatin (Type A, 275-300 bloom). During preparation, each component was screened through a 40 mesh screen before being added in the correct weight ratio to a mixing vessel. The dry materials were mixed thoroughly for 10 minutes; then, purified water was slowly added to the mixture while stirring continued. After a wet mass formed, the mixture was passed through a 20 mesh screen, and the granules were oven-dried at 40° C. for 24 hours. After the granules had dried, they were rescreened through a 20 mesh screen.

The osmotic formulation and the wax barrier formulation were compressed in a hydraulic or rotary press into a cylindrical bilayer tablet. The osmotic face of the tablet was convex, to conform to the shape of the delivery device, while the barrier face of the tablet was flat. Tabletting was conducted to produce a clean, distinct interface between the two layers.

To prepare the vessel portion (first wall section) of the device, 70 wt % cellulose acetate 320 and 30 wt % polypropylene glycol were thoroughly mixed together and were then added to the hopper of a screw extruder. The polymeric mixture was heated at 127° C. as it was extruded through the heated barrel of the extruder and into a mold for the vessel. The polymer mixture was allowed to cool after injection into the mold, after which the vessel was removed from the opened mold.

The cap portion (second wall section) of the device was prepared in the same manner as the vessel, the composition of the cap being 70 wt % cellulose acetate 320 and 30 wt % polypropylene glycol. The heated polymeric mixture was injected into a mold for the cap and allowed to cool, and the finished cap was then ejected.

To assemble the delivery device, the desired active agent formulation is placed into a completed vessel by manual or automated fill mechanisms. The osmotic engine bilayer tablet is placed into a completed cap with the convex osmotic layer pointed into the closed end of the cap and the barrier layer exposed toward the cap opening. The open end of the filled vessel is fitted inside the open end of the cap, and the two pieces are compressed together until cap, osmotic bilayer tablet and vessel fit together tightly.

EXAMPLE 2

A delivery device was prepared as in Example 1, except that the polymeric osmotic formulation was 130 mg. The assembled device was then coated with approx. 20 mg of a methacrylic acid copolymer enteric coat (Eudragit®L 100-55, Röhm Pharma).

EXAMPLE 3

A delivery device according to the present invention was prepared as follows.

The cap (second wall section) was formed by coating a gelatin capsule with a cellulose acetate-based membrane in the following manner. A coating solution composed of 5 wt % cellulose acetate 398 and polyethylene glycol 3350 (in a 95/5 weight ratio) in a solution of acetone/ethanol (in a 90/10 weight ratio) was sprayed onto a size "0" clear gelatin capsule in a Wurster coater. The capsule was coated to a membrane thickness of 3-4 mil. The capsule was then dried in a 50° C. oven to remove residual solvent, after which the two parts of the capsule were separated with their respective membrane covering intact. The short segment of the coated capsule was retained as the required cap, while the long segment was discarded.

The vessel (first wall section) was formed by machining a cylindrical container with one open end from polycarbonate polymer. The machined dimensions were such that the open end of the vessel will fit snugly within the coated gelatin cap.

To assemble the device, following the procedure of Example 1, the osmotic engine bilayer tablet from Example 1 was placed in the cap portion, the desired active agent formulation was placed in the vessel portion, the open end of the vessel portion was fitted into the open end of the cap portion, and the two pieces were compressed together to obtain a tight fit.

Another device was prepared following the above procedures, except that during manufacture of the cap portion, the gelatin capsule was coated with a cellulose acetate/polyethylene glycol membrane of 8-9 mil thickness.

EXAMPLE 4

Delivery devices were prepared as in Example 3, except that the weight ratio of cellulose acetate to polyethylene glycol in the membrane covering the cap was 80/20.

EXAMPLE 5

Nine devices from Example 1, but not containing any active agent formulation, were assembled and placed in artificial intestinal fluid (USP XIX, intestinal fluid, simulated, TS; modified herein by not including enzymes) in a shaker bath at 37° C. Marbles were also added to the fluid to provide abrasion with the devices, simulating an intestinal environment. The devices were observed to determine when the cap and vessel portions separated from each other. The resulting average release point for the devices was at 3.84 hours (SD = 0.18 hr).

EXAMPLE 6

Two enteric-coated devices from Example 2, but not containing any active agent formulation, were assembled and placed in artificial gastric fluid (USP XIX, gastric fluid, simulated, TS; modified herein by not including enzymes) for 2 hours, after which they were removed from the gastric fluid and placed in artificial intestinal fluid. The devices were observed in the intestinal fluid to determine when the cap and vessel portions separated. The resulting average release point for the two devices was at 6.33 hours.

EXAMPLE 7

Four devices from Example 3 having a cap membrane thickness of 3–4 mil and containing cardizem pellets as the active agent formulation were placed in artificial intestinal fluid and observed for separation. The devices separated and the cardizem pellets were released to the fluid environment at an average time of about 1.4 hours after placement in the fluid.

In the same manner, three devices from Example 3 having a cap membrane thickness of 8–9 mil and containing cardizem pellets were placed in the artifical intestinal fluid environment. The devices separated and the cardizem pellets were released at an average time of about 7.1 hours after placement.

EXAMPLE 8

Five devices from Example 3 having a cap membrane thickness of 8–9 mil and containing cimetidine granules as the active agent formulation were placed in artificial intestinal fluid and observed for separation. The devices separated and the cimetidine granules were released to the fluid environment at an average time of about 6.4 hours after placement in the fluid.

EXAMPLE 9

A delivery device according to the present invention having a first immediate and prolonged delivery of active agent and a second initially delayed pulse delivery of another active agent is prepared as follows.

The first osmotic engine portion of the device is a compressed trilayer tablet composed of a 50 mg wax-based barrier layer, 200 mg of a polymeric osmotic formulation (first, expansion means) and a 50 mg wax-based first partition layer.

The polymeric osmotic formulation has a composition of 59.5 wt % polyethylene oxide (Polyox ®303, Union Carbine), 29 wt % sodium chloride, 5 wt % polyacrylic acid (Carbomer ®934P, B.F. Goodrich), 5 wt % hydroxypropylmethylcellulose E-5 (Aqualon) and 1 wt % ferric oxide. During preparation, each of the above components is screened through a 40 mesh screen, and the sized components are added to a mixing vessel in the appropriate porportions. The dry components are mixed thoroughly for 10 minutes; then, ethanol is slowly added while mixing until a wet mass has formed. The wet mass is then screened through a 20 mesh screen, and the wet granules are allowed to air dry for 18 hours. After drying, the granules are passed once more through a 20 mesh screen. Magnesium stearate (0.5 wt %) is then added to the granulation and the granulation is mixed thoroughly for 5 min.

The barrier layer and the first partition layer each has a composition of 95 wt % microcrystalline wax (MF-2JH Durawax ®, Astor Wax Corp.) and 5 wt % gelatin (Type A, 250–300 bloom, Knox Gelatin). During preparation, each component is screened through a 40 mesh screen before being added in the correct weight ratio to a mixing vessel. The dry materials are then mixed thoroughly for 10 minutes, after which purified water is slowly added to the mixture while stirring is continued. After a wet mass has formed, the mixture is passed through a 20 mesh screen, and the granules are oven-dried at 40° C. for 24 hours. After the granules have dried, they are rescreened through a 20 mesh screen.

The wax formulation (50 mg) for the barrier layer, the osmotic formulation (200 mg) and the wax formulation (50 mg) for the first partition layer are compressed together in a rotary press into a cylindrical trilayer tablet with both the barrier face and the partition face of the tablet being flat. Tabletting is conducted to produce a clean, distinct interface between the three layers.

The second osmotic engine portion of the device is a compressed bilayer tablet composed of a 50 mg wax-based second partition layer or push plate and 150 mg of a polymeric osmotic formulation (second expansion means). The composition of the second osmotic formulation is the same as that for the first osmotic formulation above, and the composition of the second partition layer or push plate is the same as that for the barrier and first partition layers above. The osmotic formulation (150 mg) and the wax partition or push plate formulation (50 mg) are compressed in a rotary press into a cylindrical bilayer tablet. The osmotic face of the tablet is convex, to conform to the shape of the device, while the partition layer face of the tablet is flat. Tabletting was conducted to produce a clean, distinct interface between the two layers.

To prepare the vessel portion (first wall section) of the device, 70 wt % cellulose acetate 320 and 30 wt % polypropylene glycol are thoroughly mixed together and the mixture is added to the hopper of a screw extruder. The polymeric mixture is heated at 127° C. as it is extruded through the heated barrel of the extruder and is extruded into a mold for the vessel. The polymer mixture is allowed to cool after injection into the mold, after which the vessel is removed. An exit orifice is drilled through the closed end of the vessel.

The cap portion (second wall section) of the device is prepared in the same manner as the vessel, and having the same composition as the vessel. The heated polymeric mixture is injected into a mold for the cap and allowed to cool, and the finished cap is then ejected.

The barrier tube for the second agent chamber, having a composition of polyethylene, is prepared by placing the polyethylene is an extruder with a barrel temperature of 130° C. and extruding the material in a tube shape. After extrusion, the tube is cut to the desired length for the chamber and is allowed to cool.

To assemble the delivery device, the exit orifice in a completed vessel portion is sealed with microcrystalline wax by dipping the end in the melted wax and allowing it to cool for about 20 seconds, after which the excess wax is wiped off. The desired first active agent formulation is placed into the vessel by manual or automated fill mechanisms. An osmotic trilayer tablet is placed into the vessel with the first partition layer in contact with the first agent formulation. A barrier tube is then placed into the vessel, having its internal end flush with the trilayer tablet and its external end flush with the open end of the vessel. A ridge around the circumference of the tube fits into a corresponding locking groove in the external wall of the vessel, securing the fitted tube in place. The desired second active agent formulation is then placed into the chamber defined by the trilayer tablet and the barrier tube by manual or automated fill mechanisms. Next, an osmotic engine bilayer tablet is placed into a completed cap, with the convex osmotic layer pointed into the closed end of the cap and the second partition layer or push plate exposed toward the cap opening. The open end of the filled vessel is fitted inside the open end of the cap, and the two pieces are compressed together until cap, osmotic bilayer tablet and vessel fit together tightly.

EXAMPLE 10

A device is prepared as follows: first, an expansion means for taking-up fluid and expanding is compressed into a tablet-layered shape, then, a hydrophobic composition is compressed into a tablet-layer shape and the two layers pressed into a contacting arrangement.

The layer comprising the means for expanding comprised a hydrogel composition comprising 60 wt % poly(ethylene oxide) comprising 7,500,000 molecular weight, 29 wt % of the osmagent sodium chloride, 5 wt % poly(acrylic) acid comprising a 3,000,000 molecular weight, 5 wt % hydroxypropylalkylcellulose such as a hydroxypropylmethylcellulose of 11,200 molecular weight and 1 wt % ferric oxide. During the preparations, each of the above components are screened through a 40 mesh screen and the sized components are added to a mixing vessel in their appropriate proportions. The dry components are mixed thoroughly for 10 minutes; then ethanol is slowly added to the blend while mixing continued until a wet mass is formed in the vessel. The wet mass is next screened through a 20 mesh screen, and the wet granules are allowed to air dry for 18 hours. After drying, the granules are passed once more through a 20 mesh screen.

The barrier comprises a hydrophobic composition, for example 95 wt % micrystalline wax and 5 wt % gelatin. During preparation, each component is screened through a 40 mesh screen before being added in the correct weight ratio to a mixing vessel. The dry materials are mixed thoroughly for 10 minutes; then, purified water is slowly added to the mixture while stirring continued. After a wet mass formed, the mixture is pass through a 20 mesh screen, and the granules are oven-dried at 40° C. for 24 hours. After the granules are dried, they are rescreened through a 20 mesh screen.

The hydrogel formulation and the hydrophobic layer are compressed in a lamination press into a bilayer laminate. The hydrogel surface of the bilaminate is onvex, to conform to the shape of the device while the hydrophobic surface is flat. The bilamination is conducted to produce a clean, distinct interface between the two lamena.

To prepare the first wall section of the device, 70 wt % cellulose acetate comprising 32% acetyl content and 30 wt % poly(propylene glycol) are thoroughly mixed together and are then added to the hopper of a screw extruder. The polymeric composition is heated at 127° C. as it is extruded through the heated barrel of the extruder and into a mold. The polymer wall-forming composition is allowed to cool after injection into the mold, and after cooling the body comprising a capsule shaped is removed from the opened mold.

Next, the cap member of the capsule of the device is prepared in the same manner. The composition of the cap comprised 70 wt % cellulose acetate and 30 wt % poly(propylene glycol) to yield the semipermeable cap. Next, the cap-forming composition is injected into the mold and the cap formed is allowed to cool, and the finished cap is ejected therefrom.

The device is assembled by placing the agent formulation by automated filling into the capsule body member. Then, bilayered laminate is placed into the capsule cap member with the hydrogel lamina positioned or oriented towards the closed end of the cap and the barrier layer facing the opened end of the cap. The open end of capsule body is fitted in contacting engagement into the opened end of the cap, and the body and cap compressed together until the cap and its body fit together tightly.

EXAMPLE 11

The procedure of Example 10 is followed in this example with all conditions as described with the addition that in the example the capsule comprises a wall formed of a composition comprising a member selected from the group consisting of a cellulose alkylate, cellulose acylate, cellulose diacylate and cellulose triacylate.

EXAMPLE 12

The procedure of Example 10 if followed in this example with all conditions as described with the addition in this example the capsule comprising the body and matched cap is manufactured with a capsule wall comprising an interior composition comprising gelatin and an exterior composition comprising a member selected from the group consisting of a cellulose alkylate, cellulose acylate, cellulose diacylate and cellulose triacylate.

The above descriptions have been given for ease of understanding only. No unnecessary limitations should be understood therefrom, as modifications will be obvious to those skilled in the art.

What is claimed is:

1. A device capsule for dispensing a drug to a biological environment, wherein the device capsule comprises:
   (a) a wall comprising a member selected from the group consisting of a cellulose alkylate, cellulose acylate, cellulose diacylate and cellulose triacylate; which device capsule wall defines and surrounds:
      (i) a body member; and,
      (ii) a cap member shaped and sized for engaging the body member in closed relation; and wherein the device capsule comprises:
   (b) 10 ng to 10 g of a composition comprising a drug in the body member; and,
   (c) 10 ng to 10 g of means in the cap member for expanding and separating the capsule into the body member and cap member, when the device capsule is in operation in the environment of use, for providing the composition comprising the drug to the environment of use.

2. A device capsule for dispensing a drug to a biological environment, wherein the device capsule comprises:
   (a) a wall comprising an interior surface comprising gelatin and an exterior surface comprising a member selected from the group consisting of a cellulose alkylate, cellulose acylate, cellulose diacylate, and cellulose triacylate; said device capsule wall surrounding two members comprising:
      (i) a body member; and,
      (ii) a cap member that fits the body member in closed relation; and wherein the device capsule comprises:
   (b) 10 ng to 10 g of a composition comprising a drug in the body member; and,
   (c) 10 ng to 10 g of means in the cap member for expanding and separating the device capsule into the body member and cap member, when the device capsule is in operation in the environment of use, for providing the composition comprising the drug to the environment of use.

3. A device capsule for dispensing an active agent to an environment of use over time, the device capsule comprising two members comprising:
   (a) a body member; and, (b) a cap member, which body member and cap member fit together in closed relation; and wherein the device capsule comprises:

(c) an active agent formulation in the body member; and, (d) means in the cap member for expanding and separating the device capsule into the body member and cap member, when the device capsule is in operation in the environment of use for providing the active agent formulation to the environment of use.

4. A method for delivering a drug to a patient in need of the drug, wherein the method comprises:

(a) admitting into the patient a device capsule comprising:

(1) a wall composition comprising a member selected from the group consisting of a cellulose alkylate, cellulose acylate, cellulose diacylate and cellulose triacylate; said device capsule wall surrounding and defines:

(2) a body; and, (3) a cap for the body to form a closed relation therewith; and wherein the device capsule comprises:

(4) 10 ng to 10 g of a composition comprising the drug in the body; and, (5) 10 ng to 10 g of means in the cap for expanding and separating a closed device capsule into the body and cap;

(b) absorbing fluid from the patient into the device capsule causing the means in the cap to expand and separate the body and the cap; thereby, (c) delivering the drug to the patient over time.

5. A method for delivering a drug to a patient in need of the drug, wherein the method comprises:

(a) admitting into the patient a device capsule comprising:

(1) a wall defined by an interior surface and an exterior surface, said interior surface formed of a composition comprising gelatin, and said exterior surface formed of a composition comprising a member selected from the group consisting of a cellulose alkylate, cellulose acylate, cellulose diacylate and cellulose triacylate; said device capsule wall defining and surrounding:

(2) a body comprising an opened end; and, (3) a cap adapted to close the opened end of the body; and wherein the device capsule comprises:

(4) 10 ng to 10 g of a composition comprising a drug in the body; and, (5) 10 ng to 10 g of means in the cap for expanding and separating the device capsule into the body and cap;

(b) absorbing fluid from the patient into the device capsule causing the means to expand and separate the body and the cap; thereby, (c) delivering the drug to the patient over time.

6. A method for delivering an active agent to an environment of use, wherein the method comprises:

(a) admitting into the environment a device comprising:

(1) a body member shaped, and sized for admittance into the environment, the body comprising an open end; and, (2) a cap member, which cap member is adapted for closing the open end of the body member; said device comprising:

(3) an active agent formulation in the body member; and (4) a composition comprising a member selected from the group consisting of an osmagent and an osmopolymer in the cap member;

(b) absorbing fluid from the environment to cause composition (4) to expand and open (1) and (2), thereby, (c) delivering active agent formulation (3) to the environment of use.

7. A device capsule for dispensing a drug to a human, the device capsule comprising:

(1) a body member; and, (2) a cap member adapted to engage the body member to provide a closed device capsule; which body member and cap member comprise:

(3) a wall that defines the body member and the cap member, which wall comprises a member selected from the group consisting of a cellulose alkylate, cellulose acylate, cellulose diacylate, and cellulose triacylate; and wherein said;

(4) body member comprises a composition comprising 10 ng to 10 g of a drug; and wherein said;

(5) cap member comprises 10 ng to 10 g of means for expanding and separating the body member and the cap member, when in closed engagement in operation, in the human for providing drug to the human.

* * * * *